(12) United States Patent
Hengerer

(10) Patent No.: US 8,529,615 B2
(45) Date of Patent: Sep. 10, 2013

(54) ELEMENT THAT CAN BE FIXED IN A BLOOD VESSEL AND IS PROVIDED WITH BIOMARKERS

(75) Inventor: Arne Hengerer, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 161 days.

(21) Appl. No.: 13/042,532

(22) Filed: Mar. 8, 2011

(65) Prior Publication Data

US 2011/0224533 A1 Sep. 15, 2011

(30) Foreign Application Priority Data

Mar. 10, 2010 (DE) .......................... 10 2010 010 821

(51) Int. Cl.
*A61F 2/06* (2013.01)
(52) U.S. Cl.
USPC .................... 623/1.13; 623/1.15; 623/1.16
(58) Field of Classification Search
USPC ........ 600/407–430; 623/1–12; 606/192–195
See application file for complete search history.

(56) References Cited

U.S. PATENT DOCUMENTS

| 5,693,085 | A  | * | 12/1997 | Buirge et al. ................. 623/1.13 |
| 6,379,379 | B1 | * | 4/2002  | Wang .............................. 623/1.15 |
| 6,725,083 | B1 | * | 4/2004  | Burbank et al. .............. 600/431 |
| 7,611,462 | B2 | * | 11/2009 | Vortman et al. ............... 600/437 |
| 2005/0058688 | A1 | | 3/2005 | Boerger et al. |
| 2005/0288764 | A1 | * | 12/2005 | Snow et al. ................... 623/1.11 |
| 2008/0058715 | A1 | * | 3/2008 | Houser et al. ............ 604/103.04 |

OTHER PUBLICATIONS

DE 10 2010 010 821.9, filed Mar. 10, 2010 (not yet published).

* cited by examiner

*Primary Examiner* — Sanjay Cattungal
(74) *Attorney, Agent, or Firm* — Harness, Dickey & Pierce, P.L.C.

(57) ABSTRACT

An element is disclosed that can be fixed in a blood vessel of a living being has a base body to which a first substance and/or a second substance is/are applied at least in parts. In at least one embodiment, the first substance is determined in such a way that it can be detected from outside of the body of the living being by way of a first non-invasive detection method and reacts with at least one first biochemical substance that is released by the living being into the blood vessel during a first pathological condition of the living being, with the result that the quantity of first substance applied to the base body is reduced. The second substance is determined in such a way that it binds at least one second biochemical substance that is released by the living being into the blood vessel during a second pathological condition of the living being and the presence of the bound substance can be detected from outside of the body of the living being by way of a second non-invasive detection method.

14 Claims, 2 Drawing Sheets second substance:
1) dextran
2) polyethyleneglycol
3) amylum
4) a derivative of 1) to 3)
4) a mixture of 1) to 4)

ELEMENT THAT CAN BE FIXED IN A BLOOD VESSEL AND IS PROVIDED WITH BIOMARKERS

PRIORITY STATEMENT

The present application hereby claims priority under 35 U.S.C. §119 on German patent application number DE 10 2010 010 821.9 filed Mar. 10, 2010, the entire contents of which are hereby incorporated herein by reference.

FIELD

At least one embodiment of the present invention generally relates to an element that can be fixed in a blood vessel of a living being, the element having a base body.

BACKGROUND

Elements are generally known. In the event of heart attack, stroke and the like they are inserted in particular in the form of what is known as a stent into an occluded blood vessel in order to keep the blood vessel open once an embolism has been dissolved.

In particular in stroke patients, in about 6% of all cases a further stroke occurs after a stent has been fixed in the affected blood vessel. A further stroke of this kind must—like any other stroke—be detected as early as possible in order to be able to keep the consequences of the corresponding stroke to a minimum.

SUMMARY

At least one embodiment of the present invention is directed to creating the prerequisites for reliably detecting a further stroke or generally a pathological condition of the living being (for example a transient ischaemic attack=TIA or an inflammation) as early as possible. In particular it should be possible to reliably detect even a "minor" further stroke (or general pathological condition) which is otherwise difficult to detect.

Advantageous embodiments of the inventive element are the subject matter of the dependent claims.

With the element that can be fixed in the blood vessel of the living being it is provided according to at least one embodiment of the invention
that a first substance and/or a second substance is/are applied at least in parts to the base body,
that the first substance is determined in such a way that it can be detected from outside of the body of the living being by way of a first non-invasive detection method and reacts with at least one first biochemical substance that is released by the living being into the blood vessel during a first pathological condition of the living being, with the result that the quantity of the first substance applied to the base body is reduced,
that the second substance is determined in such a way that it binds at least one second biochemical substance that is released by the living being into the blood vessel during a second pathological condition of the living being and the presence of the bound substance can be detected from outside of the body of the living being by way of a second non-invasive detection method.

By way of the embodiment according to at least one embodiment of the invention it is achieved that it is detected directly in the body of the living being whether a stroke (or a heart attack or another pathological condition) is present or not. Because of the fact that the quantity of first substance applied to the base body is reduced, the element has in particular a type of integral behavior with regard to the pathological condition to be detected, such that even a relatively weak pathological condition can be reliably detected—even if only with a corresponding delay. The same applies to the biochemical substance that is bound by the second substance and in the event of the pathological condition accumulates on the base body and consequently becomes more concentrated.

The pathological condition can be determined as required. In many cases the first and/or the second pathological condition of the living being is/are undersupply of tissue of the living being with blood.

The base body should preferably react biochemically neither with blood nor with the blood vessel nor with other substances contained in the blood. It should therefore preferably consist of a material which has these properties. Examples of suitable materials are platinum and plastics.

In many cases the base body is embodied as a stent. The stent can in the case of the treatment of an embolism be the stent that is inserted into the affected blood vessel to keep the blood vessel open after an embolism. Alternatively it can be an additional stent. In the latter case, the inventive element can be placed at any location in the living being. It does not have to be near to the location where the pathological condition occurs (even if this is clearly possible for example and generally to be preferred).

It is possible for the first substance to be a single chemical substance which reacts with the first biochemical substance and can also be detected by way of the first non-invasive detection method. In many cases it is however easier and sometimes even absolutely necessary for the first substance to be a mixture containing a reaction substance and a marker substance. In this case only the marker substance but not the reaction substance can be detected by means of the first non-invasive detection method. The reaction substance in this case, however, is the substance which reacts as such with the biochemical substance. Because of the reaction of the reaction substance in this case the marker substance is released and washed away by blood flowing in the blood vessel.

The reaction substance and the marker substance can be determined as required. Collagen is an example of a suitable reaction substance. Nanoparticles of iron are suitable as a marker substance.

The second substance can contain in particular dextran, polyethyleneglycol, amylum or a derivative of these three substances as well as arbitrary mixtures thereof.

The first and the second non-invasive detection method can in principle be selected as desired. In many cases the first and/or the second non-invasive detection method is/are based on static and/or dynamic magnetic effects which are induced by the first substance and/or the at least one substance bound by the second substance.

BRIEF DESCRIPTION OF THE DRAWINGS

Further advantages and details will emerge from the following description of exemplary embodiments in conjunction with the drawings. These show schematically.

DETAILED DESCRIPTION OF THE EXAMPLE EMBODIMENTS

Figure 1:
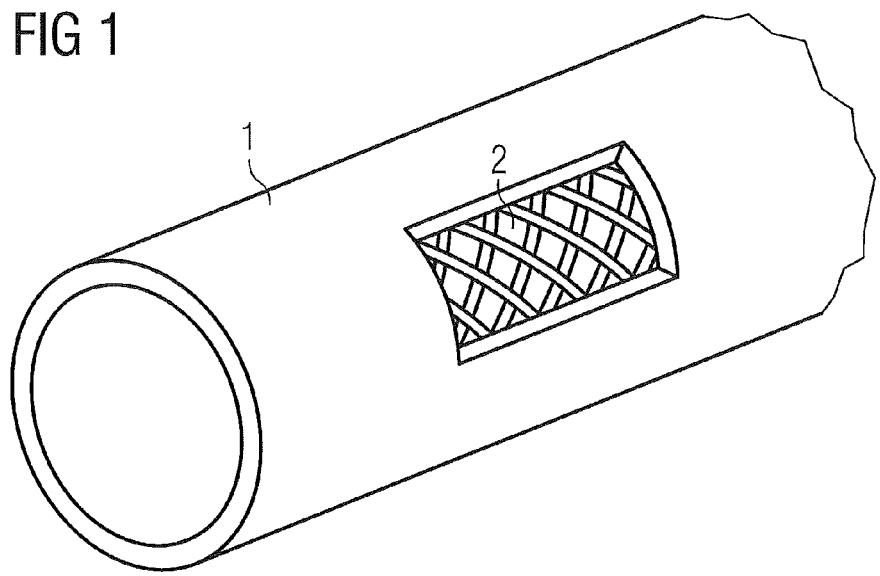
FIG. 1 a section of a blood vessel in perspective view,
FIG. 2 the section of the blood vessel of FIG. 1 in longitudinal section,
FIG. 3 the section of the blood vessel of FIG. 1 in cross-section,
FIG. 4 a possible first substance by way of example and
FIG. 5 a table with possible second substances.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 2:
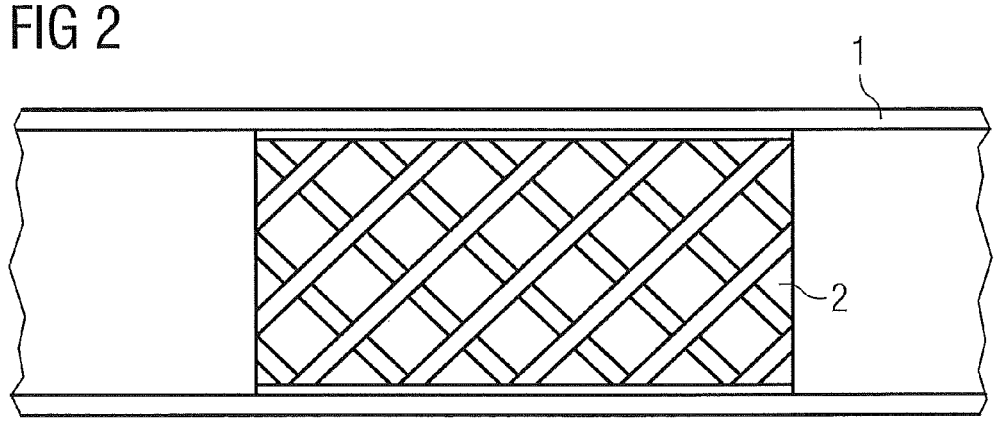
Figure 3:
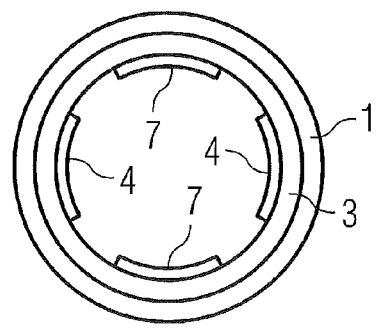

According to FIGS. 1 to 3 an element 2 is fixed in a blood vessel 1 of a living being (generally a mammal, in particular a human being). The element 2 is generally fixed in an artery of a living being. In individual cases it is however also possible for the element 2 to be fixed in a vein of the living being.

According to FIG. 1 to 3 the element 2 has a base body 3 which is preferably embodied as a stent. Stents are generally known to persons skilled in the art. They are usually either embodied according to the representation shown in FIGS. 1 to 3 as a mesh or as a simple spiral or as a combination of two spirals running in opposite directions. They generally include an inert material, i.e. a material which reacts neither with blood nor with the blood vessel 1 nor with other substances contained in blood. Corresponding materials are generally known to persons skilled in the art. Examples of suitable materials are platinum and various plastics.

A stent is generally inserted into the blood vessel 1 by way of a catheter. The procedures for inserting the stent into the blood vessel 1 and for fixing the stent in the blood vessel 1 are generally known to persons skilled in the art.

An embodiment of the present invention is explained in the following with reference to the element 2 illustrated in FIGS. 1 to 3, wherein the base body 3 is embodied as a stent. In principle the base body 3 could also have a different design. The important thing is that the element 2 can be inserted into the blood vessel 1 and fixed in the blood vessel 1.

According to FIGS. 2 and 3 a first substance 4 can be applied to the base body 3—at least in parts. In the case of a stent the first substance 4 is in particular applied on the side of the stent facing the inside of the blood vessel 1. The first substance 4 is determined in such a way that it fulfills a number of criteria.

Firstly the first substance 4 must—obviously—be tolerated by the body. In other words it must not cause any harm to the living being even though it is located in the blood vessel 1 of said living being.

Furthermore, the first substance 4 must be detectable from outside of the body of the living being by way of a non-invasive detection method even though it is located inside the blood vessel 1. It must therefore be detectable from outside of the body of the living being, whether or not the first substance 4 applied to the base body 3 is present on the base body 3 and in what quantity or concentration it may be present.

The type of non-invasive detection method for detecting the first substance 4 can be selected as required. In principle acoustic detection methods (in particular based on ultrasound), detection methods based on X-ray radiation and detection methods based on magnetic principles come into consideration. In particular, the detection method for detecting the first substance 4 is preferably based on static and/or dynamic magnetic effects which are induced by the first substance 4. An example of a dynamic magnetic effect are magnetic resonances which are excited beforehand in the first substance 4. An example of a static magnetic effect is the static magnetic field—even if very weak—that can sometimes be induced by the first substance 4 and may be detected by what is known as a SQUID (=superconducting quantum interference device).

Furthermore, the first substance 4 must react with at least one biochemical substance, the biochemical substance only being released by the living being into the blood vessel 1 when a pathological condition of the living being is present. The reaction of the first substance 4 with the biochemical substance must be such that the quantity of first substance 4 which is applied to the base body 3 is reduced due to the reaction.

In the functional sense, a distinction can be made in the first substance 4 between the marker functionality and the reaction functionality. The marker functionality signifies that the first substance 4 can be detected by means of the corresponding non-invasive detection method. The reaction functionality signifies that the first substance 4 reacts with the corresponding biochemical substance.

It is possible for the first substance 4 to be a homogeneous substance which as such has both functionalities. Alternatively, the first substance 4 according to FIG. 4 can be a mixture which contains a marker substance 5 on the one hand and a reaction substance 6 on the other hand. The marker substance 5 as such does not react in this case with the biochemical substance (otherwise the reaction substance 6 would not be required). Conversely, the reaction substance 6 as such cannot be detected by means of the non-invasive detection method used (otherwise the marker substance 5 would not be required). In such a case, provided the biochemical substance is present, the reaction substance 6 reacts with the biochemical substance with the result that its quantity is reduced. As a result the marker substance 5 which was previously held in the reaction substance 6 is released and consequently can be washed away by blood flowing in the blood vessel 1.

The marker substance 5 can be selected as required and in particular independently of the reaction substance 5. For example, the marker substance 5 according to FIG. 4 can contain nanoparticles of iron. The proportion can be as required and amount to up to 100% of the marker substance 5. In a similar way, the reaction substance 6 can be selected as required and in particular independently of the marker substance 5. If—purely by way of example—the undersupply of tissue of the living being with blood is to be detected as a pathological condition of the living being (typical cases: stroke and heart attack), the reaction substance 6 can for example contain collagen. The proportion of collagen can amount to up to 100% of the reaction substance 6. The mixing ratio of marker substance 5 and reaction substance 6 relative to each other can also be determined as required.

Purely by way of example, the effect of the last-described first substance (i.e. the mixture of iron nanoparticles as marker substance 5 and collagen as reaction substance 6) is explained briefly below.

If, in the body of the living being, the already mentioned undersupply of the tissue with blood occurs, the body releases among other things the biochemical substance MMP9 (=Metallo Matrix Protease 9) into the blood vessel 1. MMP9 reacts with collagen in such a way that collagen is broken down. As a result of the breakdown of collagen, the iron nanoparticles are released and washed away by the blood flowing in the blood vessel 1. The overall quantity of iron nanoparticles on the base body 3 is therefore reduced. This reduction can be non-invasively detected—even quantitatively—by way of corresponding magnetic methods, as described above. In the event of a sufficiently significant change an alarm can be generated to indicate that a heart attack, stroke etc. has occurred.

An embodiment of the present invention has been explained above in connection with a single first substance 4. A plurality of such substances 4 can, however, obviously also be applied to the base body 3. In the case of a plurality of first substances 4 the pathological conditions, the biochemical substance and/or the non-invasive detection method can be determined individually for each first substance 4.

According to FIGS. 1 to 3, a second substance 7 is applied to the base body 3 at least in parts. The second substance 7 can be applied to the base body 3 as an alternative to the first substance 4 (or the first substances 4). Equally it is possible for the second substance 7 to be applied to the base body 3 in addition to the first substance 4 (or the first substances 4). Like the first substance 4, the second substance 7 is preferably arranged, in particular in the case of a stent, on the side of the stent facing toward the inside of the blood vessel 1. The second substance 7 is—like the first substance 4—determined in such a way that it fulfills a number of criteria.

Firstly the second substance 7 must—like the first substance 4—be tolerated by the body. In other words it must not cause any harm.

Furthermore, the second substance 7 must bind a biochemical substance which is released by the living being into the blood vessel 1 only if a pathological condition of the living being is present. The pathological condition can be the same pathological condition as in the case of the first substance 4. Alternatively it can be a different pathological condition.

If both the first substance 4 and the second substance 7 are applied on the base body 3, it must be differentiated whether the pathological condition related to the first substance 4 and the pathological condition related to the second substance 7 are the same pathological condition or not. If they are the same pathological condition, the biochemical substance bound by means of the second substance 7 can be the same substance that reacts with the first substance 4. Alternatively it can be a different biochemical substance. If, however, the pathological conditions are different from each other, the biochemical substances must necessarily also be different from one another. This is because otherwise it would not be possible to differentiate the two pathological conditions.

The second substance 7 must furthermore be determined in such a way that the presence of the biochemical substance bound by it can be detected from outside of the body of the living being by means of a non-invasive detection method. The non-invasive detection method can be the same non-invasive detection method as in the case of the first substance 4 or alternatively another non-invasive detection method. With regard to the possible embodiments of the non-invasive detection method, the above statements made in relation to the first substance 4 can be applied analogously. It is also preferred in the case of the second substance 7 that the non-invasive detection method is based on static and/or magnetic effects which are induced by the bound biochemical substance 4. The magnetic effect can be static or alternatively dynamic in nature. The preferred non-invasive detection methods can be based, like the first substance 4, in particular on magnetic resonance techniques or on SQUID techniques.

Figures 4, 5:
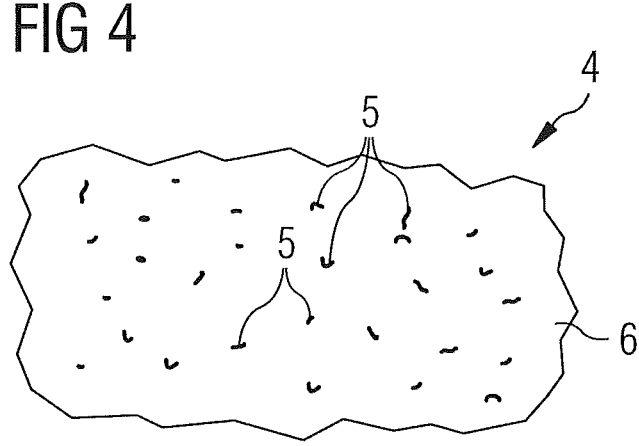

In particular in the case where the undersupply of tissue of the living being with blood is to be detected as the pathological condition of the living being by way of the second substance 7, the second substance 7 according to FIG. 5 can, for example, contain dextran, PEG (polyethyleneglycol) or amylum. Alternatively or additionally the second substance 7 can contain other polymers. Again alternatively or additionally the second substance can contain derivatives of one of these substances. Mixtures of said substances are also possible, of course.

The second substance 7 can, for example, be determined in such a way that it binds Lp-PLA2 (=lipoprotein-associated phospholipase A2). Alternatively or additionally it can bind hs-CRP (=high-sensitivity C-reactive protein). The binding of MMP9 also comes into consideration as suitable. All of these biochemical substances are released into the blood vessel 1 by the body of the living being in particular in the event of a stroke and in the event of a heart attack. An accumulation of one or even a plurality of these substances on the base body 3 is therefore an indicator of the corresponding pathological condition. The presence of the cited substance can be detected by means of the cited non-invasive detection methods based on magnetic effects.

In the same way as the first substance 4, it is possible for a plurality of second substances 7 to be applied to the base body 3. In this case the pathological condition, the biochemical substance and/or the non-invasive detection method can be determined individually for each second substance 7.

If the same pathological condition is to be detected by way of the first and second substances 4, 7, the evaluation of the corresponding non-invasively detected signals can be determined as required. In particular, a reaction can already be triggered as soon as just one of the two detected signals indicates the pathological condition. Alternatively the reaction can be triggered only once both detected signals indicate the pathological condition.

The inventive element 2 can be inserted in addition to a "normal" stent (which serves exclusively to keep the blood vessel 1 open) at any desired location in the vascular system of the living being. Alternatively the inventive element 2 can obviously also assume the "normal" functionality of a stent in addition to the inventive "biomarker functionality", i.e. the element 2 can be used in addition to keep the blood vessel 1 open.

In the case of magnetic resonance technologies the non-invasive detection method can be used, for example, with a "normal" magnetic resonance system. Alternatively, it is possible to use a so-called "handheld MRI device". Such devices are currently under development. Small SQUID devices or small MPI devices (=magnetic particle imaging) can also be used.

The above description serves solely to explain the present invention. The scope of protection of the present invention shall, however, be determined solely by the appended claims.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS 1 blood vessel
2 element
3 base body
4 first substance
5 marker substance
6 reaction substance
7 second substance

What is claimed is:

1. An element that is fixable in a blood vessel of a living being, the element comprising:
   a base body, wherein at least one of a first substance and a second substance is applied to the base body at least in parts, at least one of
   the first substance being determined in such a way as to be detectable from outside of the body of the living being by way of a first non-invasive detection method and to react with at least one first biochemical substance that is released by the living being into the blood vessel in the event of a first pathological condition of the living being, with a result that a quantity of first substance applied to the base body is reduced, and
   the second substance being determined in such a way as to bind at least one second biochemical substance that is released by the living being into the blood vessel in the event of a second pathological condition of the living being, a presence of the bound substance being detectable from outside of the body of the living being by way of a second non-invasive detection method.

2. The element as claimed in claim 1, wherein at least one of the first and the second pathological condition of the living being is the undersupply of tissue of the living being with blood.

3. The element as claimed in claim 1, wherein the base body consists of a material which reacts biochemically neither with blood nor with the blood vessel nor with other substances contained in the blood.

4. The element as claimed in claim 3, wherein the material of which the base body is composed is platinum or a plastic.

5. The element as claimed in claim 1, wherein the base body is embodied as a stent.

6. The element as claimed in claim 1, wherein
the first substance is a mixture that contains a reaction substance and a marker substance,
only the marker substance but not the reaction substance are detectable from outside of the body of the living being by way of the first non-invasive detection method,
the reaction substance reacts with the at least one first biochemical substance, and
the marker substance is released due to the reaction of the reaction substance and is washed away by blood flowing in the blood vessel.

7. The element as claimed in claim 6, wherein the reaction substance contains collagen.

8. The element as claimed in claim 6, wherein the marker substance contains iron nanoparticles.

9. The element as claimed in claim 1, wherein the second substance contains dextran, a derivative of dextran, polyethyleneglycol, a derivative of polyethyleneglycol, amylum or a derivative of amylum.

10. The element as claimed in claim 1, wherein at least one of the first and the second non-invasive detection method is based on at least one of static and dynamic magnetic effects that are induced by at least one of the first substance and the at least one substance bound by the second substance.

11. The element as claimed in claim 2, wherein the base body consists of a material which reacts biochemically neither with blood nor with the blood vessel nor with other substances contained in the blood.

12. The element as claimed in claim 11, wherein the material of which the base body is composed is platinum or a plastic.

13. The element as claimed in claim 7, wherein the marker substance contains iron nanoparticles.

14. A method, comprising:
applying, at least in parts, at least one of a first substance and a second substance to a base body of an element that is fixable in a blood vessel of a living being; and
at least one of determining the first substance in such a way as to be detectable from outside of the body of the living being by way of a first non-invasive detection method and to react with at least one first biochemical substance that is released by the living being into the blood vessel in the event of a first pathological condition of the living being, with a result that a quantity of first substance applied to the base body is reduced, and
determining the second substance in such a way as to bind at least one second biochemical substance that is released by the living being into the blood vessel in the event of a second pathological condition of the living being, a presence of the bound substance being detectable from outside of the body of the living being by way of a second non-invasive detection method.

* * * * *